United States Patent
Atkinson et al.

(10) Patent No.: US 6,913,244 B1
(45) Date of Patent: Jul. 5, 2005

(54) URINARY SLIDE VALVE

(76) Inventors: Gordon Edgar Atkinson, 123 Hammock Rd., P.O. Box 502, Anna Maria, FL (US) 34216; Mitchell Wade Yadven, 2407 Landings Cir., Bradenton, FL (US) 34209

(*) Notice: Subject to any disclaimer, the term of this patent is extended or adjusted under 35 U.S.C. 154(b) by 42 days.

(21) Appl. No.: 10/428,431

(22) Filed: May 2, 2003

(51) Int. Cl.[7] .............................................. F16K 31/00
(52) U.S. Cl. ....................... 251/343; 251/347; 251/353
(58) Field of Search ................................ 251/341, 343, 251/347, 349, 353

(56) References Cited

U.S. PATENT DOCUMENTS

| | | | |
|---|---|---|---|
| 4,055,179 A | 10/1977 | Manschot et al. | |
| 4,693,712 A | 9/1987 | Bates | |
| 4,749,103 A | * 6/1988 | Barriac | .......................... 222/48 |
| 4,934,999 A | 6/1990 | Bader | |
| 4,968,294 A | 11/1990 | Salama | |
| 5,114,398 A | 5/1992 | Trick et al. | |
| 5,156,603 A | 10/1992 | Olsen | |
| 5,234,409 A | 8/1993 | Goldberg et al. | |
| 5,310,094 A | * 5/1994 | Martinez et al. | ............. 222/212 |
| 5,630,429 A | 5/1997 | Dann | |
| 5,671,755 A | 9/1997 | Simon et al. | |
| 5,988,448 A | * 11/1999 | Foth | ...................... 222/189.09 |
| 6,027,442 A | 2/2000 | Von Iderstein | |
| 6,170,720 B1 | * 1/2001 | Gnepper et al. | ........... 222/481.5 |
| 6,183,413 B1 | 2/2001 | Migachyov | |
| 2002/0133053 A1 | 9/2002 | Latour, Jr. | |

* cited by examiner

Primary Examiner—Edward K. Look
Assistant Examiner—John K. Fristoe, Jr.
(74) Attorney, Agent, or Firm—Stevens & Showalter LLP

(57) ABSTRACT

A valve for controlling fluid flow through a flow passage. The valve includes a tubular valve body defining a longitudinal axis and having an interior surface and an exterior surface. The valve body defines first and second valve ends and a tip portion is supported on the valve body and located at the second valve end. A cap member is supported on the valve body and includes an interior surface and an exterior surface and is positioned over the second valve end for movement in a longitudinal direction parallel to the longitudinal axis. The cap member includes an open end and a closed end, and the closed end is formed by an end wall having an aperture for receiving the tip portion. The cap member is movable in a first direction toward the first valve end to position the cap member in a closed position with the tip portion extending through the aperture to prevent fluid flow through the valve body, and the cap member is movable in a second direction away from the first valve end to position the cap member in an open position with the aperture displaced from the tip member to permit fluid flow through the valve body.

16 Claims, 3 Drawing Sheets

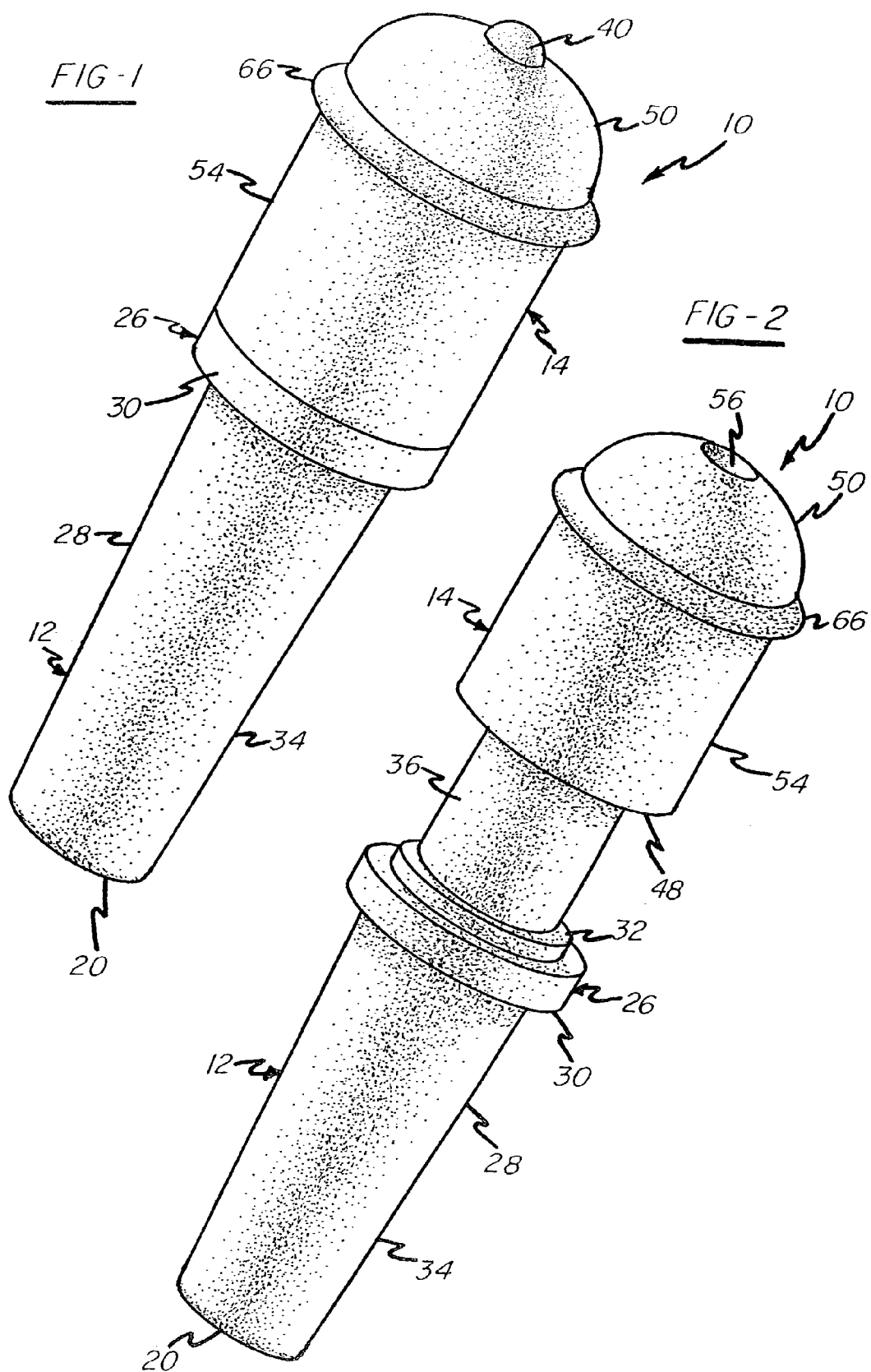

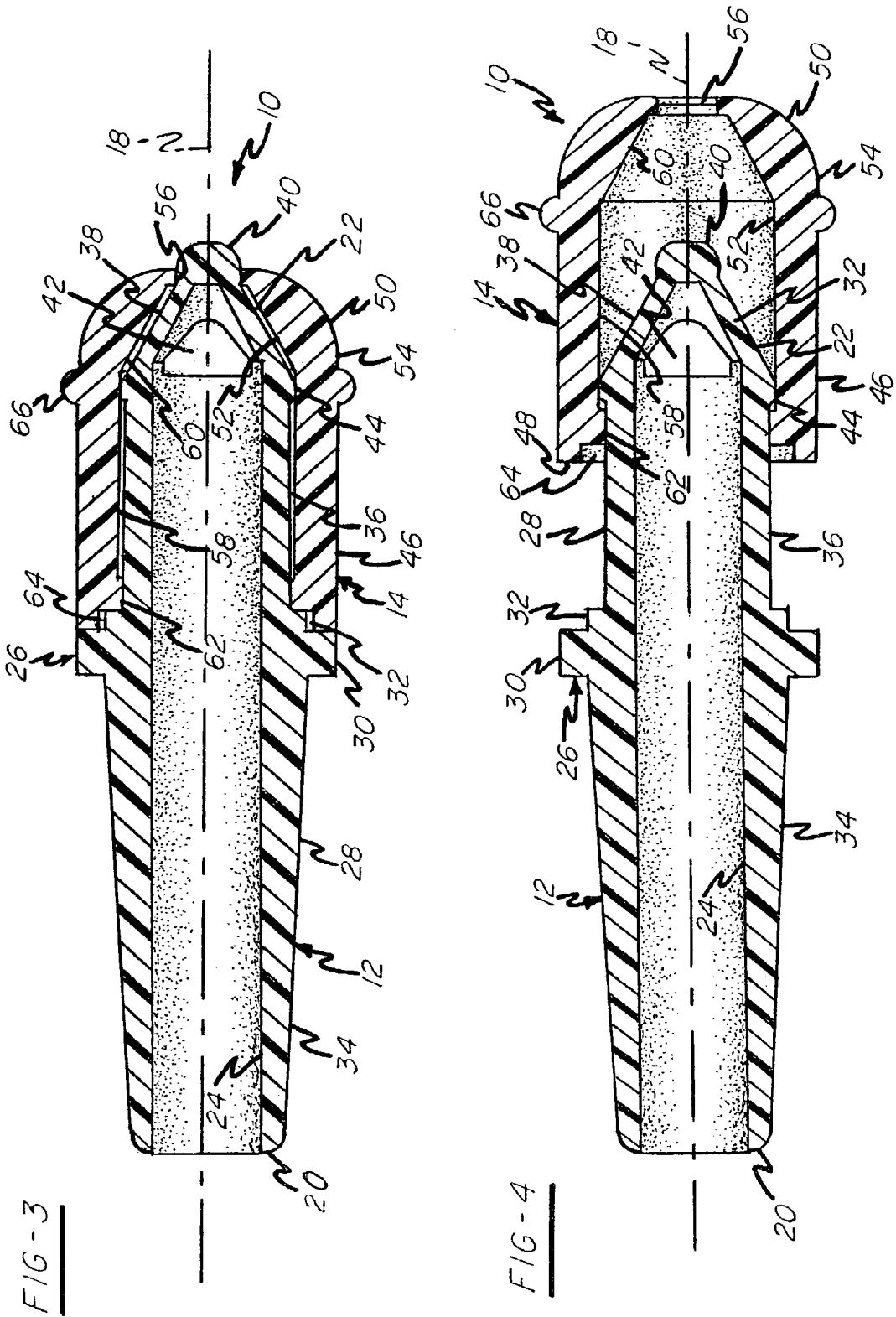

URINARY SLIDE VALVE

BACKGROUND OF THE INVENTION

1. Field of the Invention

The present invention relates to a valve for controlling fluid flow from a conduit. More particularly, the invention of the present application relates to a manually operated slide valve for inline control of fluid flow.

2. Related Prior Art

In medical liquid collection and fluid flow control systems, such as systems used to collect and/or control drainage of urine from a person's bladder, a valve is typically provided to control flow of fluid from the system. Such collection and control systems generally include a catheter having an end received in the bladder of the person, and a drainage tube connected to an opposing end of the catheter. Generally, prior art systems further include a collection bag connected to the downstream end of the drainage tube, wherein urine drains from the bladder through the catheter and drainage tube into the collection bag for retention therein. The collection bag is typically strapped to one of the person's legs and must be periodically drained as it fills.

In order to facilitate drainage of the collection bag, a valve is provided connected to a lower end of the bag, and such valves have been the subject of various prior art proposals for improvements to urinary collection and drainage systems. Such prior art designs attempt to improve on aspects of manipulation of the valve and providing a positive shut-off, among other aspects to facilitate control of the urinary collection system.

U.S. Pat. No. 4,055,179 to Manschot et al. discloses a valve for a urinary drainage container comprising a first tubular member having one end connected to the interior of a collection bag, and an opposing end including an inner tapered valve seat. A second tubular member is axially slidably positioned about the first tubular member and comprises a valve element movable into and out of engagement with the valve seat within the valve. When the valve is in an open position, fluid may flow past the valve element through the interior of a flow passageway extending from the valve element.

U.S. Pat. No. 4,693,712 to Bates discloses a valve for use with a collection container, the valve comprising a housing having a piston slidably disposed therein. The valve is moved from an open to a closed position by axially pushing the piston so that an upstream end thereof sealingly mates with an annular ridge and an inner surface of the housing. In addition, this patent addresses retrograde contamination in the fluid line by providing a bactericide tablet within the valve, which is disclosed as disinfecting the urine remaining in the valve.

U.S. Pat. No. 5,156,603 to Olsen discloses a slide valve for use with urinary collection bags. The valve includes an external tubular member and an internal tubular member which are telescopingly engaged with one another. The internal tubular member includes a valve seat for engaging a frustoconical valve body of the external tubular member to close the valve and prevent fluid flow. The valve seat and frustoconical valve body are located at an internal portion of the valve, spaced inwardly from open ends of the respective tubular members.

While the above described valves are provide for controlled fluid flow in a urinary drainage system, there remains an additional need related to such valves for improving the operation of urinary drainage systems. In particular, there remains a need for providing a valve for enabling a urinary drainage system in which a collection bag is not required. Further, there is a need for a valve which facilitates removal of residual urine, and which reduces any interior space in order to minimize growth of bacteria.

SUMMARY OF THE INVENTION

The invention of the present application provides a valve for use inline with a urinary drainage system in which the valve may be connected to a hub outlet at the end of a urinary catheter without requiring a urinary drainage or collection bag. Specifically, the invention of the present application provides a valve which permits access for thorough cleaning at the primary sealing surfaces of the valve.

In accordance with one aspect of the invention, a valve is provided for controlling fluid flow through a flow passage comprising: a tubular valve body comprising an interior surface and an exterior surface, the valve body defining a central longitudinal axis and first and second valve ends; a tip portion supported on the valve body and located at the second valve end; a cap member comprising an interior surface and an exterior surface and positioned over the second valve end for movement in a longitudinal direction parallel to the longitudinal axis; the cap member including an open end and a closed end, the closed end comprising an end wall having an aperture for receiving the tip portion; and wherein the cap member is movable in a first direction toward the first valve end to position the cap member in a closed position with the tip portion extending through the aperture to prevent fluid flow through the valve body, and the cap member is movable in a second direction away from the first valve end to position the cap member in an open position with the aperture displaced from the tip member to permit fluid flow through the valve body.

In accordance with another aspect of the invention, a valve is provided for controlling fluid flow through a flow passage comprising: a tubular valve body comprising an interior surface and an exterior surface, the valve body defining a central longitudinal axis and first and second valve ends; a tip portion supported on the valve body and located at the second valve end, a cap member comprising an interior surface and an exterior surface and positioned over the second valve end for movement in a longitudinal direction parallel to the longitudinal axis; the cap member including an open end and a closed end, the closed end comprising an end wall having an aperture for receiving the tip portion; a rear seal extending radially inwardly from the interior surface of the cap member, the rear seal defining a sliding seal for sliding along the valve body when the cap member moves in the longitudinal direction; and wherein the cap member is movable in a first direction toward the first valve end to position the cap member in a closed position with the tip portion extending through the aperture to prevent fluid flow through the valve body, and the cap member is movable in second direction away from the first valve end to position the cap member in an open position with the aperture displaced from the tip member to permit fluid flow through the valve body.

In accordance with yet a further aspect of the invention, a valve is provided for controlling fluid flow through a flow passage comprising: a tubular valve body comprising an interior surface and an exterior surface, the valve body defining a central longitudinal axis and first and second valve ends, a transition portion located at the second valve end and including flow openings for permitting fluid from the valve body through the transition portion, the transition portion angling inwardly in a direction from the first valve end toward the second valve end; a tip portion supported on the transition portion and defining a tip portion diameter; a cap member comprising an interior surface and an exterior surface and positioned over the second valve end for movement in a longitudinal direction parallel to the longitudinal axis, the cap member including an open end and a closed end, the closed end comprising an end wall having an aperture for receiving the tip portion, and the interior surface of the cap member defining a frustoconical shape adjacent the closed end for receiving the transition portion; a rear seal extending radially inwardly from the interior surface of the cap member, the rear seal defining a sliding seal for sliding along the valve body when the cap member moves in the longitudinal direction; a skirt portion extending radially outwardly from the exterior surface of the valve body for cooperating with the rear seal to prevent the cap member from sliding off the valve body as the cap member moves in the longitudinal direction, and the skirt portion engaging the interior surface of the cap member for aligning the cap member parallel to the longitudinal axis during the movement of the cap member; and wherein the cap member is movable in a first direction toward the first valve end to position the cap member in a closed position with the tip portion extending through the aperture to prevent fluid flow through the valve body, and the cap member is movable in second direction away from the first valve end to position the cap member in an open position with the aperture displaced from the tip member to permit fluid flow through the valve body.

Other features and advantages of the invention will be apparent from the following description, the accompanying drawings and the appended claims.

BRIEF DESCRIPTION OF THE DRAWINGS

FIG. 1 is a perspective view of the valve of the present application shown in a closed position;

FIG. 2 is a perspective view of the valve of the present application shown in an open position;

FIG. 3 is a cross-sectional view of the valve in the closed position;

FIG. 4 is a cross-sectional view of the valve in the open position;

DETAILED DESCRIPTION OF THE PREFERRED EMBODIMENT

Figure 5:
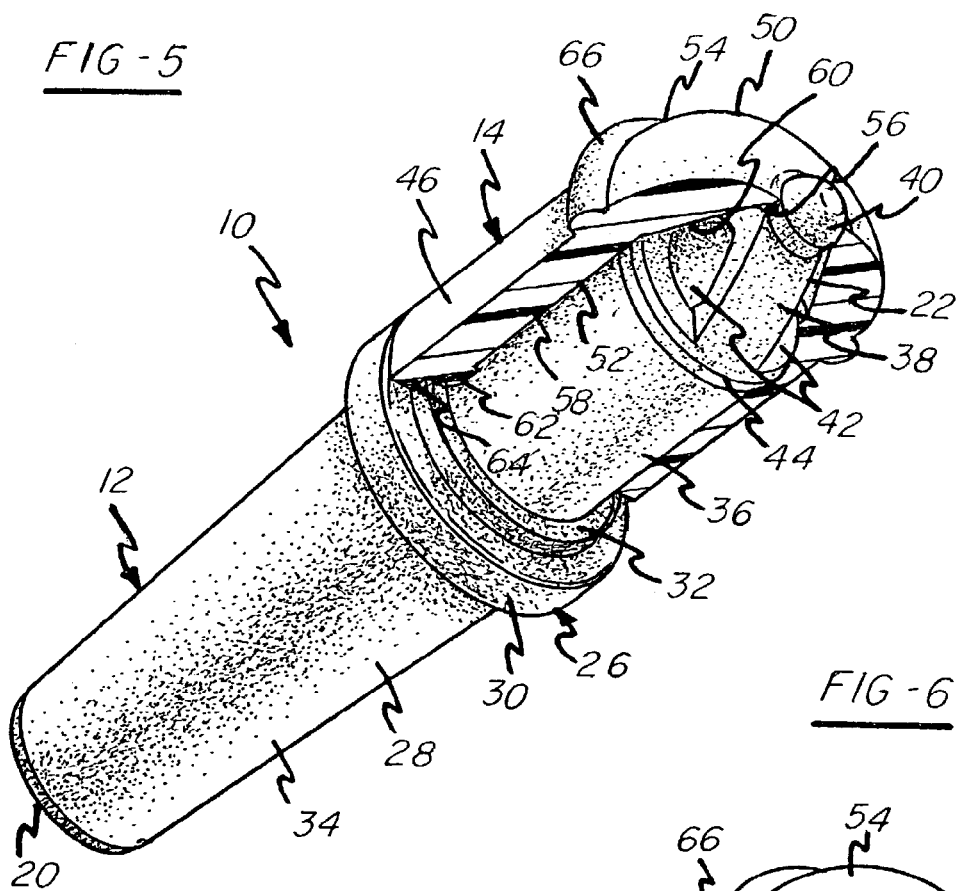
FIG. 5 is a perspective view of the valve in the closed position with the cap member shown in partial cross-section.
Figure 6:
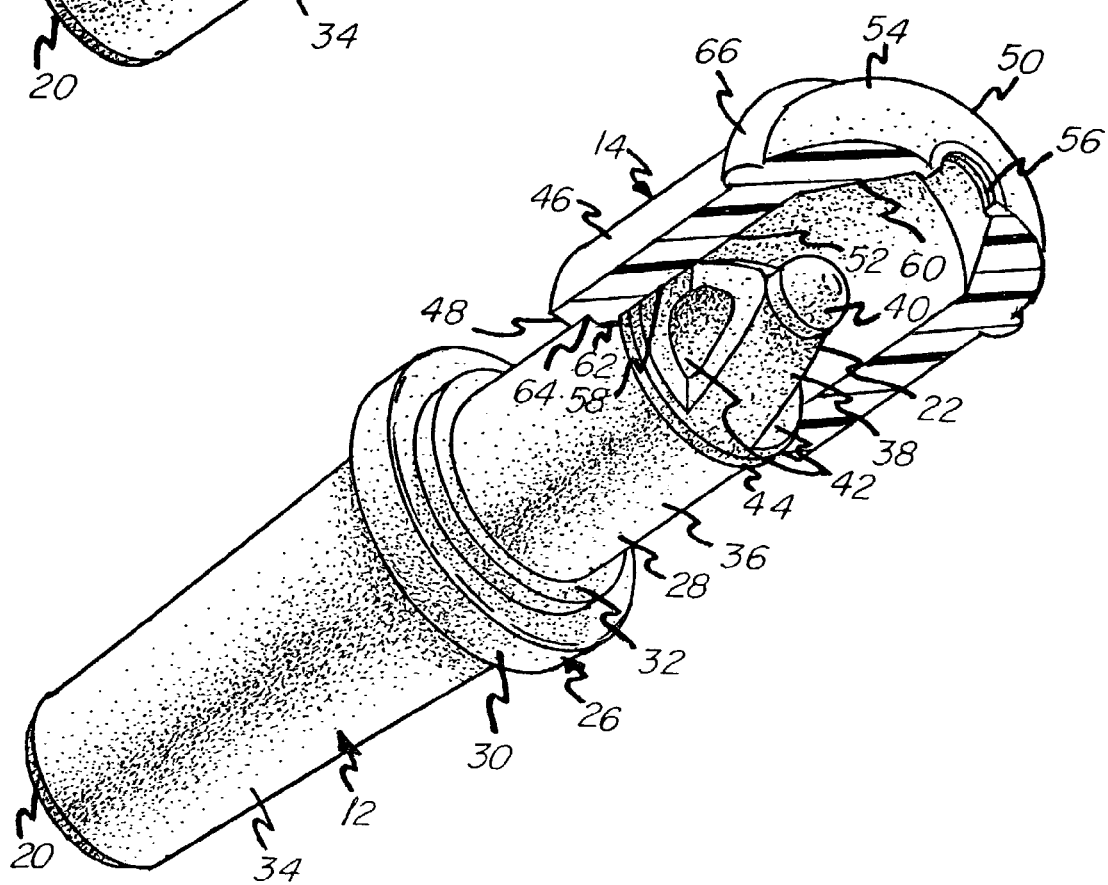
FIG. 6 is a perspective view of the valve in the open position with the cap member shown in partial cross-section.

Referring initially to FIGS. 1 and 2, the valve 10 of the present application comprises a tubular valve body 12 and a cap member 14 cooperating with and movably supported on the valve body 12. The valve body 12 and cap member 14 are formed of a plastic material having self lubricating properties, such as a polypropylene material, for purposes described in further detail below.

Referring additionally to FIGS. 3–6, the valve body 12 is configured as an elongated structure defining a central longitudinal axis 18 and a first valve end 20 comprising an inlet for the valve body 12, and a second valve end 22 comprising an outlet for the valve body 12. The valve body 12 includes an interior surface 24 defining a substantially constant interior diameter extending from the first valve end 20 to the second valve end 22 for conducting fluid flow through the valve 10.

A flange 26 extends radially outwardly from an exterior surface 28 of the valve body 12 at a location approximately midway between the first and second ends 20, 22 of the valve body 12. The flange 26 includes a main flange portion 30 and an intermediate stepped flange portion 32 wherein the intermediate stepped flange portion 32 defines a diameter which is less than a diameter of the main flange portion 30. The exterior surface 28 of the valve body 12 is tapered at an angle over a tapered portion 34 extending from the first valve end 20 to the flange 26 whereby the diameter of the exterior surface 28 increases proceeding from the first valve end 20 toward the second valve end 22. The tapered portion 34 is adapted to be inserted into a tube (not shown) such as a tube for connecting the valve 10 to a urinary catheter (not shown) having an end located in a bladder. The tapered portion 34 provides a progressively varying diameter which facilitates attachment of the valve 10 to tubes of different interior diameters, and it has been found that providing a taper of 3° results in the tapered portion 34 being easily connected to a tube, as well as provides for an acceptable removal force, while also providing a satisfactory range of diameters for fitting various tube diameters. Additionally, in accordance with a preferred application of the invention of the present application, the tapered shape of the tapered portion 34 avoids the presence of voids between the valve body 12 and an associated tube, such as may be present if a stepped surface configuration were implemented, whereby formation of spaces where urine may collect is avoided.

The exterior surface 28 of the valve body 12 includes a substantially constant diameter portion 36 extending from the flange 26 toward the second valve end 22. A transition portion 38 is located at an end of the substantially constant diameter portion 36, and angles radially inwardly extending in a direction from the first valve end 20 toward the second valve end 22. A tip portion 40 is supported at the second valve end 22 on the transition portion 38 aligned with the central longitudinal axis 18 and defining a rounded or convex shaped outer end portion. Further, the transition portion 38 is formed with a pair of fluid flow openings 42 located on opposing sides of the valve body 12 for permitting fluid to flow from the interior of the valve body 12 and out the second valve end 22. In addition, a skirt portion 44 extends radially outwardly from the exterior surface 28 of the valve body 12 at a location where the transition portion 38 adjoins the constant diameter portion 36.

The cap member 14 comprises a generally cylindrical body 46 having an open end 48 and a closed end where the closed end is defined by an end wall 50. The cap member 14 defines an interior cap member surface 52 and an exterior cap member surface 54, and the exterior surface 54 of the end wall 50 is formed with a rounded or convex shape.

An aperture 56 is formed in the end wall 50 aligned with the central longitudinal axis 18 of the valve body 12, and the cap member 14 is movable between an open position where the aperture 56 is spaced from the tip portion 40 to a closed position where the tip portion 40 is engaged through the aperture 56. It should be noted that the aperture 56 is formed with a diameter which is slightly smaller than the diameter of the tip portion 40 such that a sealing interference fit is created between the tip portion 40 and the aperture 56 when the cap member 14 is in the closed position.

The interior cap member surface 52 defines a substantially constant diameter portion 58 and a frustoconical portion 60. The constant diameter portion 58 defines a diameter which is approximately the same as the diameter of the skirt portion 44 wherein the constant diameter portion 58 of the cap member 14 moves in sliding contact with the skirt portion 44 during movement of the cap member 14 between the open position and the closed position.

A rear seal 62 is provided extending radially inwardly from the interior cap member surface 52 adjacent to the open end 48 of the cap member 14. The rear seal 62 defines a diameter which is slightly less than the diameter of the constant diameter portion 36 of the valve body 12, and forms a sliding interference fit between the cap member 14 and the valve body 12, which seals the open end 48 of the cap member 14 to the valve body 12 for preventing fluid from leaking out of the valve 10 at the location of the rear seal 62. The rear seal 62 further operates in combination with the skirt portion 44 to position the interior cap member surface 52 in slightly spaced relation from the exterior surface 28 of the valve body 12, while maintaining the cap member 14 aligned generally parallel to the central longitudinal axis 18 during longitudinal movement of the cap member 14. Accordingly, the contact areas between the cap member 14 and the valve body 12 are minimized to reduce the frictional forces resisting movement of the cap member 14 relative to the valve body 12, while providing for guided movement of the cap member 14 between the open and closed positions. Also, it should be noted that the spacing between the interior cap member surface 52 and the exterior surface 28 of the valve body 12 is very small, i.e., on the order of 0.02 inches, in order to minimize any available space for fluid accumulation.

Further, the interior cap member surface 52 formed by the frustoconical shaped portion 60 extends into the end wall 50 adjacent the closed end. The angle defined by the frustoconical portion 60 substantially matches an angle defined by the transition portion 38 such that a space between the transition portion 38 and the end wall 50 of the cap member 14 is also minimized.

In positioning the valve 10 in the closed position, as illustrated in FIGS. 1, 3 and 5, the cap member 14 is moved in a first direction to position the tip portion 40 of the valve body 12 extending through and slightly beyond the aperture 56 in the cap member 14 to define a seal preventing fluid flow from the valve body 12. The open end 48 of the cap member 14 is positioned on the flange 26 wherein a groove 64 is defined in the edge of the cap member 14 adjacent the rear seal 62 for receiving the intermediate stepped flange portion 32 and defining a seat for the open end 48 of the cap member 14 in the closed position. In this position, the interference fit between the tip portion 40 and the aperture 56 of the cap member 14, and between the rear seal 62 and the exterior surface 36 of the valve body 12 provide a substantial frictional force for maintaining the cap member 14 in the closed position.

In order to open the valve 10, a user twists or rotates the cap member 14 slightly relative to the valve body 12, in order to release the frictional forces between the two parts, and at the same time initiates longitudinal sliding movement of the cap member 14 in a second direction toward the open position wherein the self lubricating nature of the polypropylene material facilitates sliding movement after the initial friction force is overcome. Movement of the cap member 14 to the open position is limited by engagement of the rear seal 62 against the skirt portion 44 (see FIGS. 4 and 6). Further, in order to facilitate gripping the cap member 14, a radially extending rib 66 is provided on the exterior cap member surface 54, extending circumferentially around the cap member 14 adjacent the end wall 50. The rib 66 is formed with a rounded semi-spherical shape which is easily manually gripped by the fingers of the user.

It should be noted that the seal defined between the end of the tip portion 40 and the end wall 50 of the cap member 14 is intentionally located at an exposed location which is accessible to a user. Further, the convex shape provided to both the tip portion 40 and the exterior cap member surface 54 of the end wall 50 is such that substantially any portion of the surfaces of the tip portion 40 and end wall 50 exposed to the atmosphere will be accessible for wiping and cleaning after the valve 10 is closed following use. Such a cleaning operation may be performed using an isopropyl alcohol pad or using mild soap and water to wipe the exposed surfaces clean. Accordingly, the invention of the present application is configured to avoid growth of bacteria which may otherwise readily occur on any exposed surface containing residual urine.

Additionally, the invention of the present application further contemplates deterring growth of bacteria on the valve surfaces by coating the surfaces of the valve body 12 and the cap member 14 with an antibacterial material. Alternatively, an antibacterial material may be included in the plastic material, i.e., included with the polypropylene material, at the time of molding the valve body 12 and the cap member 14.

It should also be understood that the valve 10 of the present invention may be incorporated in other inline valve applications, such as incorporating the valve inline between two fluid conduits, including a fluid conduit attached to either end of the valve.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A urinary valve for controlling fluid flow through a urinary catheter flow passage comprising:

a tubular valve body comprising an interior surface and an exterior surface, said valve body defining a central longitudinal axis and first and second valve ends;

a tip portion supported on said valve body and located at said second valve end;

a cap member comprising an inner surface and an outer surface and positioned over said second valve end for movement in a longitudinal direction parallel to said longitudinal axis;

said cap member including an open end and a closed end, said closed end comprising an end wall defining an outwardly facing exterior surface and having an aperture for receiving said tip portion, said aperture comprising a diameter smaller than the diameter of said tip portion;

a flange extending radially outwardly from said outer surface of said valve body adjacent said open end of said cap member;

said exterior surface of said valve body being tapered adjacent said first valve end, on a side of said flange opposite said cap member, and defining an increasing exterior diameter in a direction from said first valve end toward said second valve end; and wherein said cap member is movable in a first direction toward said first valve end to position said cap member in a closed position with said tip portion extending through said aperture, and forming an exposed wipable surface at an interference seal around the circumference of said tip portion at the exterior surface of the cap member, to prevent fluid flow of liquid and air past said interference seal, and said cap member is movable in a second direction away from said first valve end to position said cap member in an open position with said aperture displaced from said tip member to permit fluid flow through said valve body.

2. The valve of claim 1 wherein said inner surface of said cap member defines an interior cap diameter, and said tip portion and said aperture define a diameter smaller than said interior cap diameter.

3. The valve of claim 1 wherein said valve body includes a skirt portion extending radially outwardly from said exterior surface of said valve body and said cap member includes a rear element extending radially inwardly from said inner surface of said cap member at said open end of said cap member, said rear element cooperating with said skirt portion to prevent said cap member from sliding off said valve body as said cap member moves to said open position.

4. The valve of claim 3 wherein said rear element defines a seal comprising an interior diameter smaller than an exterior diameter of said valve body adjacent to said rear seal such that an interference fit is defined between said rear element and said valve body, said rear element defining a sliding seal for sliding along said valve body when said cap member slides between said open and closed positions.

5. The valve of claim 1 including a transition portion supporting said tip portion at said second valve end, and including flow openings in said transition portion for permitting fluid flow from said valve body through said aperture in said cap member.

6. The valve of claim 5 wherein said transition portion angles inwardly in a direction from said first valve end toward said second valve end, and said inner surface of said cap member defines a frustoconical shape adjacent said closed end for receiving said transition portion.

7. The valve of claim 1 wherein said exterior surface of said cap member, at said closed end, defines a convex shape.

8. The valve of claim 1 wherein said tip portion includes a smoothly convex shaped end extending outwardly beyond said interference seal and said exterior surface of said cap member when said cap member is located in said closed position.

9. The valve of claim 1 wherein said open end of said cap member engages said flange when said cap member is located in said closed position.

10. The valve of claim 1 including a rib extending circumferentially around said cap member adjacent said closed end for facilitating a user manually grasping and moving said cap member relative to said valve body.

11. The valve of claim 1 comprising an antibacterial material on said surfaces of said valve body and said cap member for preventing bacterial growth on fluid contacting surfaces of said valve.

12. A urinary valve for controlling fluid flow through a urinary catheter flow passage comprising:
  a tubular valve body comprising an interior surface and an exterior surface, said valve body defining a central longitudinal axis and first and second valve ends;
  a tip portion supported on said valve body and located at said second valve end;
  a cap member comprising an inner surface and an outer surface and positioned over said second valve end for movement in a longitudinal direction parallel to said longitudinal axis;
  said cap member including an open end and a closed end, said closed end comprising an end wall defining an outwardly facing exterior surface and having an aperture for receiving said tip portion, said aperture comprising a diameter smaller than the diameter of said tip portion;
  a flange extending radially outwardly from said outer surface of said valve body adjacent said open end of said cap member; said exterior surface of said valve body being tapered adjacent said first valve end, on a side of said flange opposite said cap member, and defining an increasing exterior diameter in a direction from said first valve end toward said second valve end;
  a transition portion supporting said tip portion at said second valve end, and including flow openings in said transition portion for permitting fluid flow from said valve body through said aperture in said cap member, said transition portion angling inwardly in a direction from said first valve end toward said second valve end;
  said inner surface of said cap member defining a cylindrical portion and a frustoconical portion defined by a surface angling inwardly from said cylindrical portion toward said end wall, where an angle defined by said frustoconical portion substantially matches an angle defined by said transition portion;
  a rear seal extending radially inwardly from said inner surface of said cap member, said rear seal defining a sliding seal for sliding along said valve body when said cap member moves in said longitudinal direction; and
  wherein said cap member is movable in a first direction toward said first valve end to position said cap member in a closed position with said tip portion extending through said aperture and with said frustoconical portion closely adjacent to said transition portion, and forming an exposed wipable surface at an interference seal around the circumference of said tip portion at the exterior surface of the cap member, to prevent fluid flow of liquid and air past said interference seal, and said cap member is movable in a second direction away from said first valve end to position said cap member in an open position with said aperture displaced from said tip member to permit fluid flow through said valve body.

13. The valve of claim 12 wherein said rear seal defines an interior diameter smaller than an exterior diameter of said valve body adjacent to said rear seal such that an interference fit is defined between said rear seal and said valve body.

14. The valve of claim 13 wherein said valve body includes a skirt portion extending radially outwardly from said exterior surface of said valve body for cooperating with said rear seal to prevent said cap member from sliding off said valve body as said cap member moves to said open position.

15. The valve of claim 12 wherein said exterior surface of said cap member, at said closed end, defines a convex shape, and said tip portion includes a smoothly convex shaped end extending outwardly beyond said interference seal at said exterior surface of said cap member when said cap member is located in said closed position.

16. A urinary valve for controlling fluid flow through a urinary catheter flow passage comprising:
  a tubular valve body comprising an interior surface and an exterior surface; said valve body defining a central longitudinal axis and first and second valve ends;
  a transition portion located at said second valve end and including flow openings for permitting fluid from said valve body through said transition portion, said transition portion angling inwardly in a direction from said first valve end toward said second valve end;

a tip portion supported on said transition portion and defining a tip portion diameter;

a cap member comprising an inner surface and an outer surface and positioned over said second valve end for movement in a longitudinal direction parallel to said longitudinal axis;

said cap member including an open end and a closed end, said closed end comprising an end wall defining an outwardly facing exterior surface and having an aperture for receiving said tip portion, said aperture comprising a diameter smaller than the diameter of said tip portion, and said inner surface of said cap member defining a frustoconical shape adjacent said closed end for receiving said transition portion;

a rear seal extending radially inwardly from said inner surface of said cap member, said rear seal defining a sliding seal for sliding along said valve body when said cap member moves in said longitudinal direction;

a skirt portion extending radially outwardly from said exterior surface of said valve body for cooperating with said rear seal to prevent said cap member from sliding off said valve body as said cap member moves in said longitudinal direction, and said skirt portion engaging said inner surface of said cap member for aligning said cap member parallel to said longitudinal axis during said movement of said cap member;

a flange extending radially outwardly from said outer surface of said valve body adjacent said open end of said cap member;

said exterior surface of said valve body being tapered adjacent said first valve end, on a side of said flange opposite said cap member, and defining an increasing exterior diameter in a direction from said first valve end toward said second valve end; and wherein said cap member is movable in a first direction toward said first valve end to position said cap member in a closed position with said tip portion extending through said aperture, and forming an exposed wipable surface at an interference seal around the circumference of said tip portion at the exterior surface of the cap member, to prevent fluid flow of liquid and air past said interference seal, and said cap member is movable in a second direction away from said first valve end to position said cap member in an open position with said aperture displaced from said tip member to permit fluid flow through said valve body.

* * * * *